US011213255B2

(12) United States Patent
Hikida

(10) Patent No.: US 11,213,255 B2
(45) Date of Patent: Jan. 4, 2022

(54) INFORMATION PROCESSING DEVICE, INFORMATION PROCESSING METHOD, AND RECORDING MEDIUM STORING INFORMATION PROCESSING PROGRAM

(71) Applicant: Ricoh Company, Ltd., Tokyo (JP)

(72) Inventor: Satoshi Hikida, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 687 days.

(21) Appl. No.: 16/021,431

(22) Filed: Jun. 28, 2018

(65) Prior Publication Data

US 2019/0000389 A1 Jan. 3, 2019

(30) Foreign Application Priority Data

Jul. 3, 2017 (JP) .............................. JP2017-130704

(51) Int. Cl.
 *A61B 5/00* (2006.01)
 *G01R 33/565* (2006.01)
 (Continued)

(52) U.S. Cl.
 CPC ............ *A61B 5/7203* (2013.01); *A61B 5/245* (2021.01); *A61B 5/4094* (2013.01); *A61B 5/742* (2013.01);
 (Continued)

(58) Field of Classification Search
 CPC ..... A61B 5/7203; A61B 5/742; A61B 5/4094; A61B 5/04008; G01R 33/565;
 (Continued)

(56) References Cited

U.S. PATENT DOCUMENTS

| 6,697,660 | B1 | 2/2004 | Robinson |
| 2004/0097802 | A1* | 5/2004 | Cohen ................. A61B 5/4094 600/411 |
| 2008/0304731 | A1 | 12/2008 | Kimura |

FOREIGN PATENT DOCUMENTS

| JP | 2000-088940 | 3/2000 |
| JP | 2007-240270 | 9/2007 |

(Continued)

OTHER PUBLICATIONS

K.Sekihara, Y.Kawabata, S.Ushio, S.Sumiya, S.Kawabata, Y.Adachi, S.S.Nagarajan, "Dual signal subspace projection (DSSP): a novel algorithm for removing large interference in biomagnetic measurements", published Apr. 11, 2016, Journal of Neural Engineering vol. 13 No. 3, (2016).

(Continued)

*Primary Examiner* — Peter Luong
(74) *Attorney, Agent, or Firm* — Xsensus LLP

(57) ABSTRACT

An information processing device, an information processing method, and a recording medium storing an information processing program. The information processing device and the information processing method include obtaining measurement data, accepting a specification of time in the measurement data as a specified time, reducing noise from the measurement data using each one of a plurality of methods, evaluating a result of noise reduction at the specified time, the noise reduction being performed using each one of the plurality of methods, and selecting one of the plurality of methods based on the evaluated result of noise reduction. The recording medium storing the information processing program for causing a computer to execute the information processing method.

9 Claims, 4 Drawing Sheets

(51) Int. Cl.
   *G01R 33/00*   (2006.01)
   *G01R 33/035*  (2006.01)
   *G01R 33/10*   (2006.01)
   *A61B 5/245*   (2021.01)

(52) U.S. Cl.
   CPC ....... *G01R 33/0029* (2013.01); *G01R 33/035* (2013.01); *G01R 33/10* (2013.01); *G01R 33/565* (2013.01); *G01R 33/56509* (2013.01)

(58) Field of Classification Search
   CPC .......... G01R 33/56509; G01R 33/0029; G01R 33/0035; G01R 33/10
   See application file for complete search history.

(56) References Cited

FOREIGN PATENT DOCUMENTS

| JP | 2008-161637 | 7/2008 |
|----|-------------|--------|
| JP | 2018-004286 | 1/2018 |
| WO | WO2004/081595 A1 | 9/2004 |
| WO | WO2005/030051 A1 | 4/2005 |
| WO | WO2005/067789 A1 | 7/2005 |
| WO | WO2005/078467 A1 | 8/2005 |
| WO | WO2006/114473 A1 | 11/2006 |
| WO | WO2011/117471 A1 | 9/2011 |
| WO | WO2012/004458 A1 | 1/2012 |

OTHER PUBLICATIONS

Extended European Search Report dated Jan. 8, 2019 in European Patent Application No. 18178707.8, citing documents AA, AB and AX therein, 13 pages Adachi, Y., et al., "Recent advancements in the SQUID magnetospinogram system", Topical Review, Superconductor Science and Technology, vol. 30 No. 6, May 2017, XP020316624, pp. 1-16.

* cited by examiner

INFORMATION PROCESSING DEVICE, INFORMATION PROCESSING METHOD, AND RECORDING MEDIUM STORING INFORMATION PROCESSING PROGRAM

CROSS-REFERENCE TO RELATED APPLICATION

This patent application is based on and claims priority pursuant to 35 U.S.C. § 119(a) to Japanese Patent Application No. 2017-130704, filed on Jul. 3, 2017, in the Japan Patent Office, the entire disclosure of which is hereby incorporated by reference herein.

BACKGROUND

Technical Field

Embodiments of the present disclosure relate to an information processing device, an information processing method, and a recording medium storing an information processing program.

Background Art

Technologies to remove external noise when biomagnetism is measured in magnetoencephalography are desired.

Methods are known in the art in which multiple data signals are extracted from the measured signals and temporally overlapping components in the extracted signals are removed as noise. Dual signal subspace projection (DSSP) is one example of such methods.

DSSP relates to technologies to remove external noise by signal processing, and includes algorithms in which two data signals are extracted from the measured signals using the sensitivity matrix of a sensor and temporally overlapping components in the extracted signals are removed as noise.

SUMMARY

Embodiments of the present disclosure described herein provide an information processing device, an information processing method, and a recording medium storing an information processing program. The information processing device and the information processing method include obtaining measurement data, accepting a specification of time in the measurement data as a specified time, reducing noise from the measurement data using each one of a plurality of methods, evaluating a result of noise reduction at the specified time, the noise reduction being performed using each one of the plurality of methods, and selecting one of the plurality of methods based on the evaluated result of noise reduction. The recording medium storing the information processing program for causing a computer to execute the information processing method.

BRIEF DESCRIPTION OF THE DRAWINGS

A more complete appreciation of exemplary embodiments and the many attendant advantages thereof will be readily obtained as the same becomes better understood by reference to the following detailed description when considered in connection with the accompanying drawings.

Figure 1:
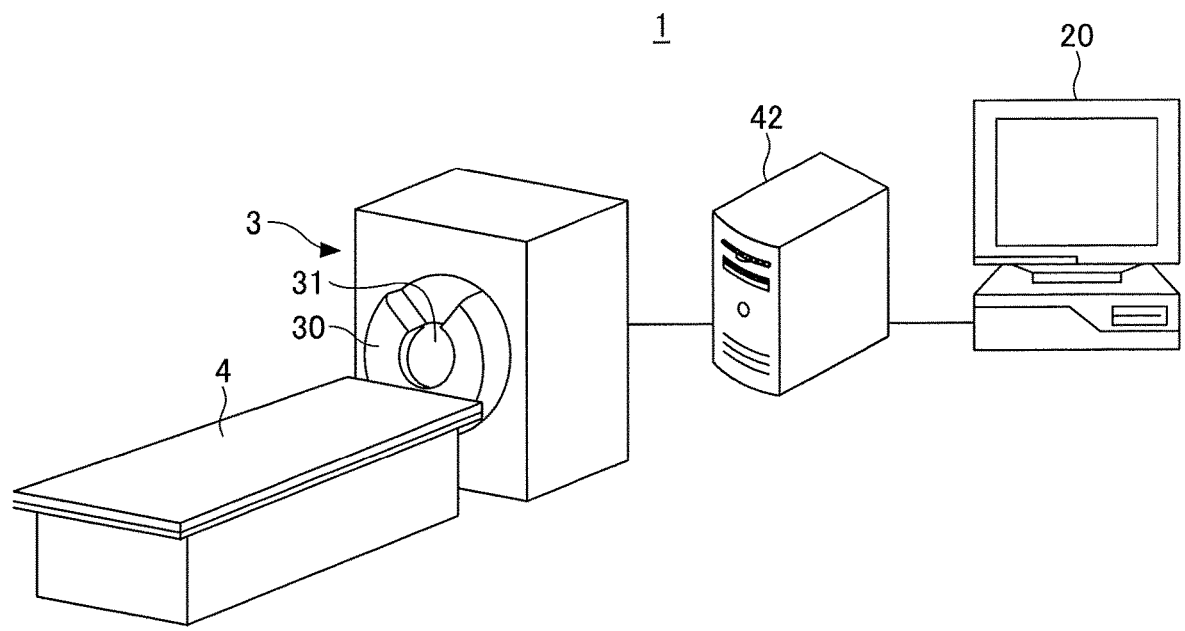
FIG. 1 is a diagram illustrating a configuration of an information processing system according to an embodiment of the present disclosure.

The accompanying drawings are intended to depict exemplary embodiments of the present disclosure and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present disclosure. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments shown in the drawings, specific terminology is employed for the sake of clarity. However, the present disclosure is not intended to be limited to the specific terminology so selected and it is to be understood that each specific element includes all technical equivalents that have the same structure, operate in a similar manner, and achieve a similar result.

In the following description, illustrative embodiments will be described with reference to acts and symbolic representations of operations (e.g., in the form of flowcharts) that may be implemented as program modules or functional processes including routines, programs, objects, components, data structures, etc., that perform particular tasks or implement particular abstract data types and may be implemented using existing hardware at existing network elements or control nodes. Such existing hardware may include one or more central processing units (CPUs), digital signal processors (DSPs), application-specific integrated circuits (ASICs), field programmable gate arrays (FPGAs), computers or the like. These terms in general may be collectively referred to as processors.

Unless specifically stated otherwise, or as is apparent from the discussion, terms such as "processing" or "computing" or "calculating" or "determining" or "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Embodiments of the present disclosure are described below with reference to the drawings.

<System Configuration>

FIG. 1 is a diagram illustrating a configuration of an information processing system 1 according to an embodiment of the present disclosure.

In FIG. 1, the information processing system 1 measures various kinds of biomedical signals such as magneto-encephalography (MEG) signals and electro-encephalography (EEG) signals, and displays the results of measurement. The information processing system 1 includes a measurement device 3, a data recording server 42, and an information processing device 20. The information processing device 20 has a monitoring display 26 (see FIG. 2) on which the signal data obtained in the measurement (measurement data) and the analytical results are displayed. In FIG. 1 according to the present embodiment, the data recording server 42 and the information processing device 20 are shown as separate units. However, the data recording server 42 may at least partially be integrated into the information processing device 20.

A subject lies on a measurement table 4 on his or her back with electrodes (or sensors) attached to his or her head to measure the brain waves, and puts his or her head into a hollow 31 of a Dewar 30 of the measurement device 3. The Dewar 30 is a vacuum container of liquid helium that can be used at very low temperatures, and multiple magnetic sensors for measuring brain magnetism are disposed on the inner surface of the hollow 31 of the Dewar 30. The measurement device 3 collects the brain-wave signals and the brain-magnetism signals through the electrodes and the magnetic sensors, respectively, and outputs the collected biomedical signals (measurement data) to the data recording server 42. The measurement data recorded in the data recording server 42 is read and displayed by the information processing device 20, and is analyzed by the information processing device 20. As known in the art, the Dewar 30 integrated with magnetic sensors and the measurement table 4 is inside a magnetically shielded room. However, for the sake of explanatory convenience, such a magnetically shielded room is omitted in FIG. 1.

The information processing device 20 synchronizes and displays the waveforms of the brain-magnetism signals obtained through the multiple magnetic sensors and the waveform of the brain-wave signals obtained through the multiple electrodes on the same time axis. The brain-wave signals indicate the inter-electrode voltage value obtained for the electrical activity of nerve cells (i.e., the flow of ionic charge caused at the dendrites of neurons during synaptic transmission). Moreover, the brain-magnetism signals indicate minute changes in magnetic field caused by the electrical activity of the brain. The magnetic field of the brain is detected by a high-sensitivity superconducting quantum interference device (SQUID).

<Hardware Configuration>

Figure 2:
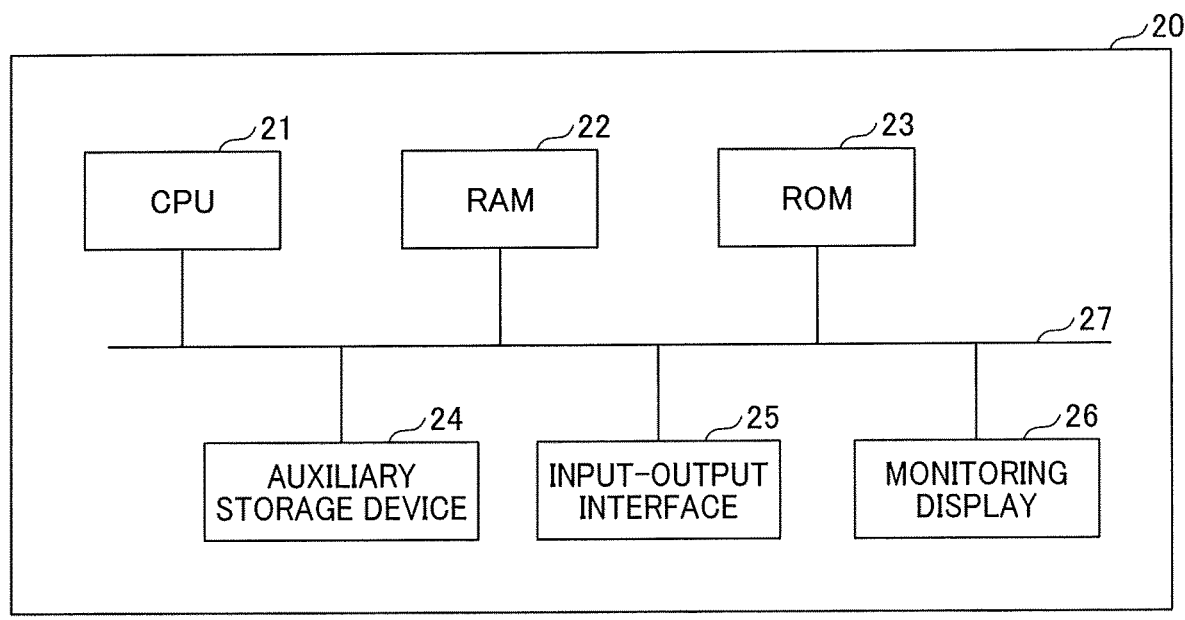
FIG. 2 is a block diagram illustrating a hardware configuration of an information processing device according to an embodiment of the present disclosure.

FIG. 2 is a diagram illustrating a hardware configuration of the information processing device 20 according to the present embodiment. The information processing device 20 is provided with a central processing unit (CPU) (processor) 21, a random access memory (RAM) 22, a read only memory (ROM) 23, an auxiliary storage device 24, an input-output (I/O) interface 25, and a monitoring display (display) 26, and these elements are interconnected through a bus 27.

The CPU 21 controls the entire operation of the information processing device 20, and performs various kinds of information processing. Moreover, the CPU 21 executes an information processing program stored in the ROM 23 or the auxiliary storage device 24, to control the display of the measurement recording screen and the analyzing screen.

A recording medium is provided with an information processing program to implement the processes performed by the information processing device 20. For example, such an information processing program may be read from a recording medium, and installed in the auxiliary storage device 24 through the input-output interface 25. However, it is not necessary for the program to be read from a recording medium and installed, and the program may be downloaded from another external computer through the network.

The RAM 22 is used as a work area of the CPU 21, and may include a nonvolatile RAM in which a desired control parameter or desired data are stored. For example, the ROM 23 stores a basic input and output program. The ROM 23 may also store an information processing program according to the present embodiment.

The auxiliary storage device 24 is a storage device such as a solid state disk (SSD) and a hard disk drive (HDD), and stores, for example, a control program to control the operation of the information processing device 20, various kinds of data used to operate the information processing device 20, and files.

The input-output interface 25 is provided with both a user interface such as a touch panel, a keyboard, a display screen, and an operation key and a communication interface that takes in data from various kinds of sensors or the data recording server 42 and outputs the analyzed data to another external electronic device.

The measurement recording screen and the analyzing screen are displayed on the monitoring display 26, and the screen of the monitoring display 26 is updated in response to input and output operation through the input-output interface 25.

Next, a functional configuration of the information processing device 20 according to the present embodiment is described with reference to FIG. 3.

Figure 3:
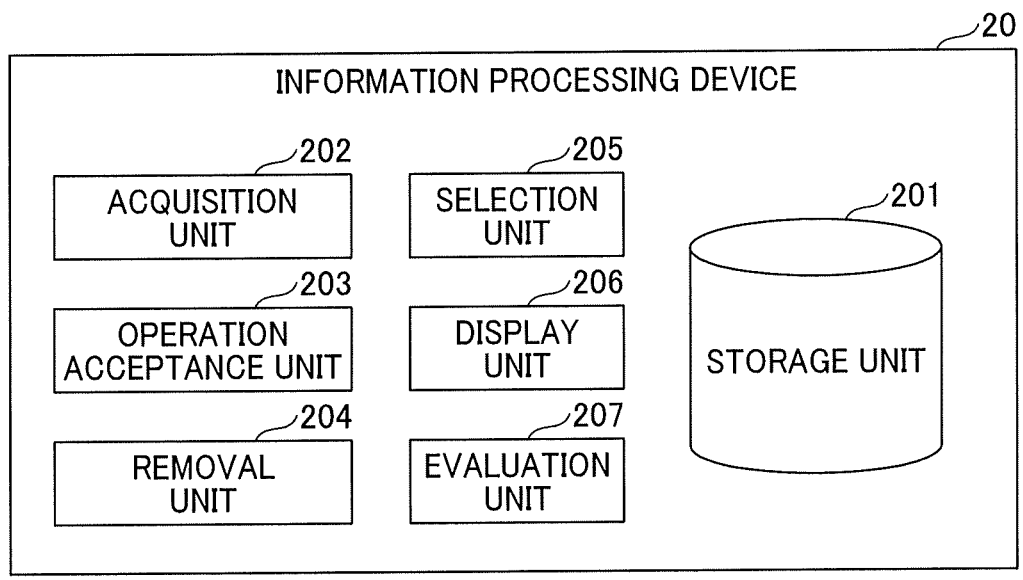
FIG. 3 is a block diagram illustrating a functional configuration of an information processing device according to an embodiment of the present disclosure.

FIG. 3 is a diagram illustrating a functional configuration of the information processing device 20 according to the present embodiment. The information processing device 20 includes a storage unit 201. For example, the storage unit 201 is implemented by an auxiliary storage device 24.

Moreover, the information processing device 20 includes an acquisition unit 202, an operation acceptance unit 203, a removal unit 204, a selection unit 205, a display unit 206, and an evaluation unit 207. These elements are implemented by the processes performed by the CPU 21 of the information processing device 20 using one or more programs installed in the information processing device 20.

The acquisition unit 202 obtains the measurement data obtained by the measurement device 3 from the data recording server 42. Moreover, the acquisition unit 202 obtains the number of sensors in a Dewar 30, the positions of the respective sensors, and the sensitivity data or the like from the measurement device 3 (or a storage device such as the data recording server 42) through the data recording server 42.

On the screen that displays the brain waves, the operation acceptance unit 203 receives the specification of time at which a spike in waveform is recorded due to epilepsy from a user who is, for example, a doctor.

The removal unit 204 removes noise from the measurement data obtained by the acquisition unit 202, using each one of a plurality of methods. Note that such a plurality of methods may include, for example, at least one of multiple methods where the algorithms are different from each other, multiple methods where the same algorithm is used in common but the strength is different from each other, and multiple methods where both the algorithms and strength are different from each other.

For example, a plurality of methods may be used where the optimal value varies depending on the conditions such as the number of dimensionalities to be processed and dealt with, the threshold for a correlation coefficient, and the sensitivity matrix of a sensor to be used (wherein at least one of the parameters is different from each other).

Regarding the data from which noise has been removed by the removal unit 204 using each one of the multiple methods, the evaluation unit 207 evaluates the result of noise reduction at the time received through the operation acceptance unit 203.

The selection unit 205 selects one of the multiple methods based on the evaluation made by the evaluation unit 207.

The display unit 206 uses the method selected by the selection unit 205 and controls the monitoring display 26 to display the measurement data from which noise has been removed by the removal unit 204. Moreover, the display unit 206 displays the screen image to which the method selected by the selection unit 205 is set as the initial value.

Next, the processes that are performed by the information processing device 20 according to the present embodiment are described with reference to FIG. 4.

Figure 4:
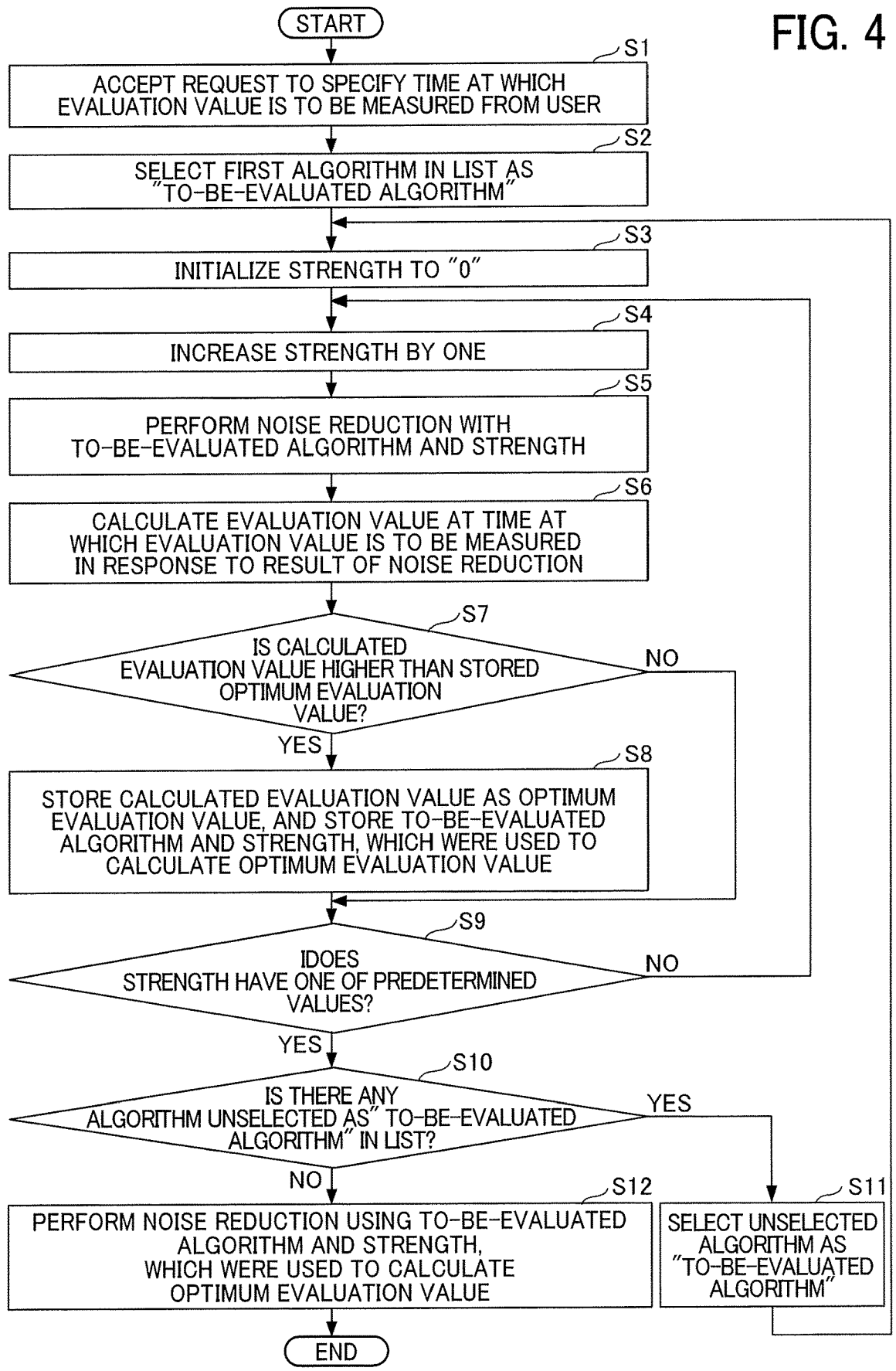
FIG. 4 is a flowchart of the processes performed by an information processing device according to an embodiment of the present disclosure.

FIG. 4 is a flowchart of the processes performed by the information processing device 20, according to the present embodiment. The following description illustrates an example in which one of the multiple methods where both the algorithms and strength are different from each other is selected.

In a step S1, the operation acceptance unit 203 accepts a request from a user to specify a time at which an evaluation value is to be measured. In the step S1, as a time at which an evaluation value is to be measured, for example, the peak time of a spike caused by epilepsy, which is read from the waveform of the brain waves, is specified.

Epilepsy is a disorder of the brain characterized by repeated seizures (epileptic seizures) of the nerve cells of the brain in an abrupt manner by intense electrical excitation. When an epileptic seizure takes place, a number of nerve cells produce electricity at the same time, and thus large electric current flows and a specific spike is measured in waveform of the brain waves.

Subsequently, the selection unit 205 initializes the optimum evaluation value to "0" and selects the first algorithm in a prescribed list as a "to-be-evaluated algorithm" (a step S2). Here, each of the algorithms included in the list may be, for example, the DSSP, or a method (signal subspace projection (SSP) of time) in which multiple data signals are extracted from the measured signals, using the sensitivity matrix of a sensor, and temporally overlapping components in the extracted signals are removed as noise by the signal subspace projection (SSP).

Subsequently, the selection unit 205 initializes the strength to "0" in the to-be-evaluated algorithm (setting) (step S3).

Subsequently, the selection unit 205 increases the value of strength by one in the to-be-evaluated algorithm (step S4).

Subsequently, the removal unit 204 performs noise reduction with the to-be-evaluated algorithm and the strength (step S5). Note that the noise reduction will be described later in detail.

Subsequently, in response to the result of the noise reduction, the evaluation unit 207 calculates and obtains the evaluation value at the user-specified time at which the evaluation value is to be measured (step S6). In the step S6, in order to calculate and obtain the evaluation value, for example, the evaluation unit 207 may estimate a dipole at the time when an evaluation value is to be measured. In such a configuration, assuming that the center of the brain is the predetermined position, the evaluation unit 207 may schematically perform estimation where the brain is regarded as a sphere filled with electrically-conductive solution, using the Sarvas formula. Due to this configuration, the speed of the dipole estimation processes can further be enhanced.

Alternatively, the evaluation unit 207 may adopt a method such as spatial filtering and sparse coding.

Then, the evaluation unit 207 may calculate and obtain the evaluation value for the estimated result, using goodness of fit (GoF). In such a configuration, the evaluation unit 207 may calculate the degree of approximation between the magnetic field (i.e., an example of a "prescribed magnetic field") calculated from the signal source estimated assuming that the signal source is a single dipole and the magnetic field caused by the dipole estimated from the actually observed and measured measurement data, and use the calculated degree of approximation as a reliability index for estimation. Then, the GoF is calculated and obtained using Formula 1 given below.

[Formula 1]

$$1 - \Sigma(X_i - Y_i)^2 / \Sigma X_i^2 \qquad (1)$$

In Formula 1, Xi denotes the actually measured magnetic field strength and Yi denotes the estimated magnetic field intensity. Instead of the GoF, the evaluation value may be calculated using, for example, a correlation coefficient.

Subsequently, the selection unit 205 determines whether or not the calculated evaluation value is higher than the stored optimum evaluation value (step S7).

When the calculated evaluation value is not higher than the stored optimum evaluation value ("NO" in the step S7), the process proceeds to a step S9, which will be described later in detail.

When the calculated evaluation value is higher than the stored optimum evaluation value ("YES" in the step S7), the selection unit 205 stores the calculated evaluation value in the storage unit 201 as the optimum evaluation value, and stores the to-be-evaluated algorithm and the strength, which were used to calculate the optimum evaluation value, in the storage unit 201 (step S8).

Subsequently, the selection unit 205 determines whether or not the strength in the to-be-evaluated algorithm has one of the predetermined values (the step S9).

When the strength has none of the predetermined values ("NO" in the step S9), the process shifts to the step S4.

When the strength has one of the predetermined values ("YES" in the step S9), the selection unit 205 determines whether or not there is any algorithm unselected as the "to-be-evaluated algorithm" in the above list (a step S10).

When there is an unselected algorithm registered in the list ("YES" in the step S10), the selection unit 205 selects the unselected algorithm as the "to-be-evaluated algorithm" (step S11), and the process shifts to the step S3.

When there is no unselected algorithm registered in the list ("NO" in the step S10), the removal unit 204 performs noise reduction using the to-be-evaluated algorithm and the strength, which were used to calculate the optimum evaluation value and stored in the storage unit 201 in the step S8 (a step S12), and terminates the processes. Note also that the data from which noise has been removed in the step S12 is displayed on the screen of the monitoring display 26 by the display unit 206.

Instead of performing noise reduction by the removal unit 204, the result of the noise reduction in the step S5, where the to-be-evaluated algorithm and strength are used, may be stored in advance and output in the step S12.

Next, an example of the noise reduction in the step S5 by the removal unit 204 is described. In the following description, a method is described in which two data signals are extracted from the signals measured and obtained by the sensors, using the lead field matrix that indicates the sensitivity matrix of a sensor and temporally overlapping components in the extracted signals are removed as noise using the SSP are removed as noise using the SSP.

Firstly, the removal unit 204 calculates and obtains a pair of symmetric matrices G1 and G2, using Formula 2 and Formula 3 given below, respectively.

[Formula 2]

$$G_1 = L_1 L_1^T \qquad (2)$$

[Formula 3]

$$G_2 = L_2 L_2^T \qquad (3)$$

In Formula 3, L1 and L2 are lead field matrices that are determined based on the above two data signals, and XT indicates a transpose of matrix X.

Subsequently, the removal unit 204 calculates P1 and P2 using Formula 4 and Formula 5 given below, respectively.

[Formula 4]

$$SVD(G_1) = P_1 Q_1 P_1^T \qquad (4)$$

[Formula 5]

$$SVD(G_2) = P_2 Q_2 P_2^T \qquad (5)$$

In Formula 5, SVG(X) indicates singular value decomposition of X.

Subsequently, B1 and B2 are calculated and obtained based on the obtained P1 and P2, using Formula 6 and Formula 7 given below, respectively.

[Formula 6]

$$B_1 = (I - P_1) B \qquad (6)$$

[Formula 7]

$$B_2 = P_2 B_1 \qquad (7)$$

In Formula 6, I denotes a unit matrix.

Subsequently, the removal unit 204 calculates and obtains characteristic values S and V for B2, using Formula 8 given below.

[Formula 8]

$$SVD(B_2) = USV^T \qquad (8)$$

Subsequently, the removal unit 204 removes noise using Formula 9 given below.

[Formula 9]

$$Y = X(I - V_n V_n^T) \qquad (9)$$

In Formula 9, Y denotes a signal from which noise has been removed, and X denotes a mixed signal including noise (measurement data). Moreover, Vn indicates, for example, the first to n-th V components in descending order of the characteristic values S. In Formula 9, n denotes an example of the above strength.

Figure 5:
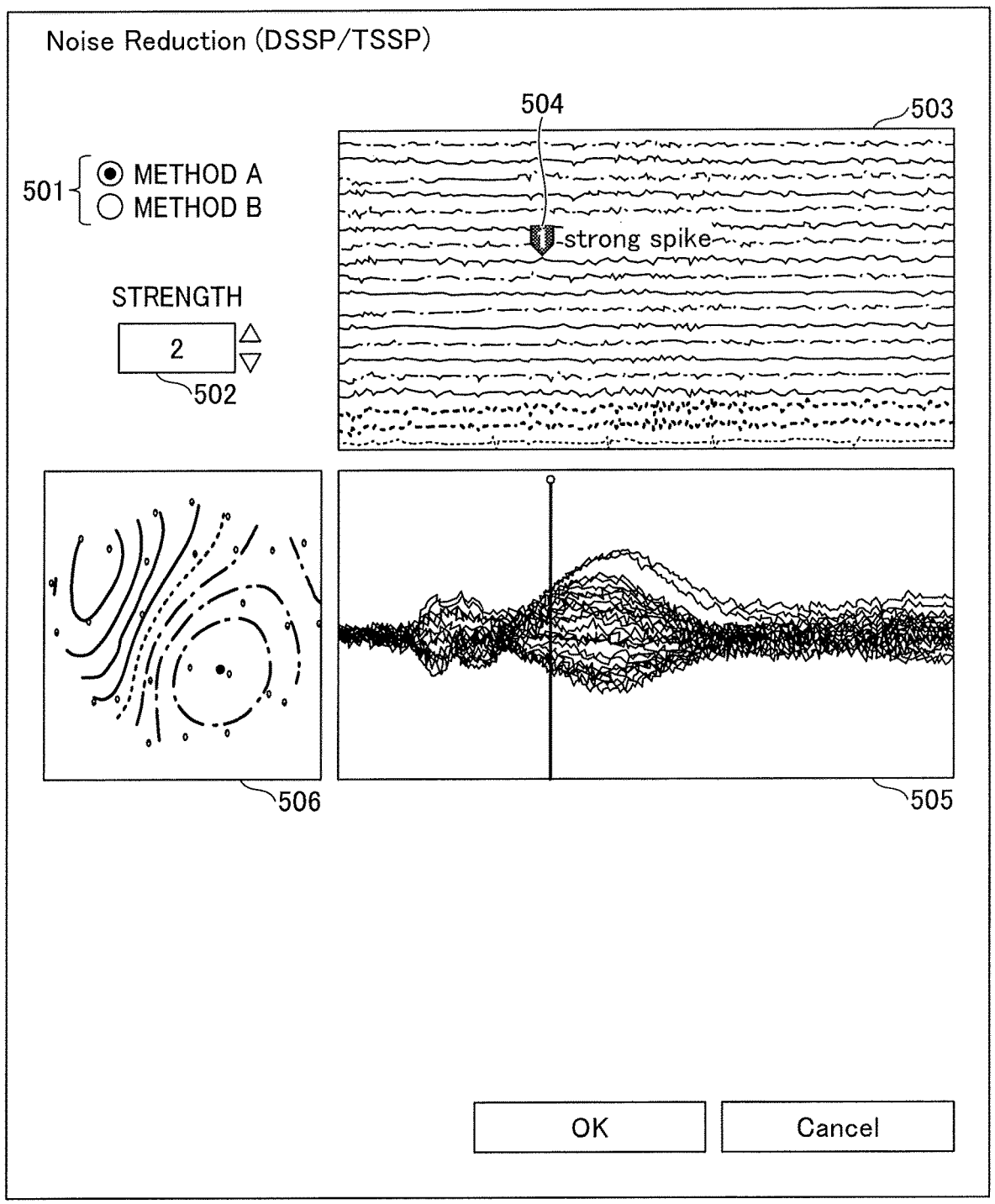
FIG. 5 is a diagram illustrating a display screen of an information processing device according to an embodiment of the present disclosure.

FIG. 5 is a diagram illustrating the display screen of the information processing device 20, according to the present embodiment. In the example illustrated in FIG. 5, the operation of selecting the noise reduction algorithms in Method A and Method B to be used by the removal unit 204 is accepted at the radio buttons for selection 501. Note that the Method A and Method B in FIG. 5 correspond to the DSSP and SSP of time.

In the input field 502 where the level of noise reduction is to be specified, the inputting (selecting) of the strength in the noise reduction algorithms to be used by the removal unit 204 is accepted.

In an area 503, the measurement data obtained by the acquisition unit 202 is displayed. In the example illustrated in FIG. 5, the vertical axis indicates the intensity of an electrical signal (amplitude), and the horizontal axis indicates time. In the step S1 as described above, in the area 503, the operation acceptance unit 203 accepts a request to specify a time at which an evaluation value is to be measured from a user. An icon (annotation) 504 indicates a position specified by a user on the area 503. The time at which an evaluation value is to be measured is specified by the position of the icon 504 in the horizontal axis.

The selection unit 205 sets the algorithm of the optimum evaluation value and the strength, which were used in the above step S12, in radio buttons for selection 501 and an input field 502 as illustrated in FIG. 5, respectively, as the initial values, and controls the display unit 206 to display the algorithms and the strength.

The values set to the radio buttons for selection 501 and the input field 502 can be edited by a user. When the values are edited, the operation acceptance unit 203 accepts the edited set values, and the removal unit 204 performs noise reduction with the algorithms and the strength that are selected according to the edited set values. Due to this configuration, the user-selected values for the parameters can be selected in view of the optimal value that is automatically selected by the system as the initial value.

The display unit 206 displays in an area 505 the data of the dipole estimated based on the results of noise reduction that is performed according to the values set to the radio buttons for selection 501 and the input field 502, respectively, by the removal unit 204. Moreover, the display unit 206 displays in an area 506 a magnetic-field contour map based on the results of noise reduction that is performed according to the values set to the radio buttons for selection 501 and the input field 502, respectively, by the removal unit 204.

In the known technologies to remove external noise in measurement, a user has to manually set various kinds of parameters in such removing processes. For example, in a method where multiple data signals are extracted from the measured signals and temporally overlapping components in the extracted signals are removed as noise, the optimal strength varies depending on the type of noise. Accordingly, a user has to choose the value of strength by trial and error. For example, in the DSSP, the strength is determined depending on the degree of temporal correlation between the bases of two data signals extracted from the measured signals. However, the optimal degree of correlation varies depending on the type of noise. Accordingly, the optimal strength cannot always be determined based only on the degree of correlation.

Moreover, when a plurality of noise reduction methods is available, the type of noise that can efficiently be reduced varies depending on the selected noise reduction method. For this reason, noise can more efficiently be reduced when an optimal method is selected from among the multiple noise reduction methods. Conventionally, a user has to select an optimal noise reduction method by trial and error.

According to the embodiments as described above, noise is reduced from the measurement data using each one of a plurality of methods, and one of the multiple methods is selected based on the evaluation of the result of noise reduction at selected time. Due to this configuration, external noise can more easily be reduced in measurement.

For example, the multiple functional units of the information processing device 20 may implemented by cloud computing that is configured by one or more computers (one or more processors).

Numerous additional modifications and variations are possible in light of the above teachings. It is therefore to be understood that within the scope of the appended claims, the disclosure of the present invention may be practiced otherwise than as specifically described herein. For example, elements and/or features of different illustrative embodiments may be combined with each other and/or substituted for each other within the scope of this disclosure and appended claims.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

What is claimed is:

1. An information processing device, comprising:
   circuitry configured to
   acquire biomedical measurement data of a patient, the biomedical measurement data being obtained from biomedical sensors;
   accept a specification of a specified time within the biomedical measurement data;
   separately apply a plurality of separate noise-reduction methods to the biomedical measurement data to reduce noise in the biomedical measurement data thereby generating a corresponding plurality of noise-reduced data sets, one for each of the plurality of noise-reduction methods;
   evaluate each of the plurality of noise-reduced data sets at the specified time within the biomedical measurement data to generate a plurality of evaluation values, one for each of the plurality of noise-reduction methods;
   select a particular method of the plurality of noise-reduction methods based on the plurality of evaluation values; and
   apply the selected particular method to the biomedical measurement data to generate noise-reduced biomedical measurement data,
   wherein the circuitry is further configured to cause a display to display a screen image to which a selected one of the plurality of noise-reduction methods is set as an initial value.

2. The information processing device according to claim 1, wherein the circuitry is further configured to apply the plurality of noise-reduction methods to the biomedical measurement data, wherein at least one of an algorithm and a strength of the noise reduction is different from each other for each of the plurality of noise-reduction methods.

3. The information processing device according to claim 1, wherein the circuitry is further configured to:
   calculate a degree of approximation between a prescribed magnetic field and a magnetic field caused by a dipole estimated from the obtained biomedical measurement data, from which the noise has been removed using each one of the plurality of noise-reduction methods, at the specified time; and
   generate the plurality of evaluation values using the calculated degree of approximation.

4. The information processing device of claim 1, wherein the circuitry is further configured to accept the specified time from input by a user, and calculate the plurality of evaluation values at only the specified time within the biomedical measurement data.

5. The information processing device of claim 1, wherein the circuitry is further configured to display the noise-reduced biomedical measurement data.

6. The information processing device of claim 5, wherein the circuitry is further configured to display the noise-reduced biomedical measurement data and display, within the noise-reduced biomedical measurement data, an icon indicating the specified time.

7. The information processing device of claim 1, wherein the biomedical measurement data is one of magneto-encephalography (MEG) data and electro-encephalography (EEG) data of a brain of the patient.

8. An information processing device, comprising:
   circuitry configured to
   acquire biomedical measurement data of a patient, the biomedical measurement data being obtained from biomedical sensors;
   accept a specification of a specified time within the biomedical measurement data;
   separately apply a plurality of separate noise-reduction methods to the biomedical measurement data to reduce noise in the biomedical measurement data thereby generating a corresponding plurality of noise-reduced data sets, one for each of the plurality of noise-reduction methods;
   evaluate each of the plurality of noise-reduced data sets at the specified time within the biomedical measurement data to generate a plurality of evaluation values, one for each of the plurality of noise-reduction methods;
   select a particular method of the plurality of noise-reduction methods based on the plurality of evaluation values; and
   apply the selected particular method to the biomedical measurement data to generate noise-reduced biomedical measurement data,
   wherein the biomedical measurement data is data of a brain wave, and
   wherein the circuitry is further configured to cause a display to display a screen displaying the brain wave, and receive the specification of the specified time, which is a time at which a spike in a waveform of the brain wave is recorded due to an epileptic seizure.

9. A method of processing information, the method comprising:
   acquiring biomedical measurement data of a patient, the biomedical measurement data being obtained from biomedical sensors;
   accepting a specification of a specified time within the biomedical measurement data;
   separately applying a plurality of separate noise-reduction methods to the biomedical measurement data to reduce noise in the biomedical measurement data thereby generating a corresponding plurality of noise-reduced data sets, one for each of the plurality of noise-reduction methods;

evaluating each of the plurality of noise-reduced data sets at the specified time within the biomedical measurement data, to generate a plurality of evaluation values, one for each of the plurality of noise-reduction methods;

selecting a particular method of the plurality of noise-reduction methods based on the plurality of evaluation values;

applying the selected particular method to the biomedical measurement data to generate noise-reduced biomedical measurement data; and displaying a screen image to which a selected one of the plurality of noise-reduction methods is set as an initial value.

* * * * *